(12) United States Patent
Wegelin et al.

(10) Patent No.: US 10,045,667 B2
(45) Date of Patent: *Aug. 14, 2018

(54) POINT-OF-CARE HYGIENE COMPLIANCE MODULE

(71) Applicant: GOJO Industries, Inc., Akron, OH (US)

(72) Inventors: Jackson W. Wegelin, Stow, OH (US); Matthew J. Archer, Aurora, OH (US)

(73) Assignee: GOJO INDUSTRIES, INC., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/386,087

(22) Filed: Dec. 21, 2016

(65) Prior Publication Data

US 2017/0100002 A1  Apr. 13, 2017

Related U.S. Application Data

(62) Division of application No. 14/995,481, filed on Jan. 14, 2016, which is a division of application No. (Continued)

(51) Int. Cl.
*B67D 7/58* (2010.01)
*A47K 5/12* (2006.01)
*G06M 1/276* (2006.01)

(52) U.S. Cl.
CPC .......... *A47K 5/1217* (2013.01); *A47K 5/1205* (2013.01); *G06M 1/276* (2013.01)

(58) Field of Classification Search
CPC ... A47K 5/1217; A47K 5/1205; A47K 5/1211
(Continued)

(56) References Cited

U.S. PATENT DOCUMENTS 3,589,563 A * 6/1971 Carragan ............... H03K 17/28
222/648
4,932,624 A    6/1990 Holm
(Continued)

FOREIGN PATENT DOCUMENTS

DE     202004013101 U1    12/2004
EP          0940110 A1     9/1999
(Continued)

OTHER PUBLICATIONS

EP Search Report cited in EP Application No. 17185264.3 dated Nov. 17, 2017, 10 pgs.

*Primary Examiner* — Jeremy W Carroll
(74) *Attorney, Agent, or Firm* — Cooper Legal Group, LLC

(57) ABSTRACT

A point-of-care hygiene compliance module includes a housing that is adapted to be attached to a dispensing container that dispenses material through a dispensing nozzle when actuated. The housing includes a pivoting actuation arm that is configured so as to be placed in operative contact with the dispensing nozzle. Thus, when the actuation arm is actuated, material is dispensed from the dispensing container, and a switch in operative contact with the actuation arm is actuated. The triggering of the switch updates a count value that is maintained by a controller, which may then be displayed or acquired by a remote computer to assess the amount of usage of the dispensing container.

20 Claims, 12 Drawing Sheets

Related U.S. Application Data

13/833,525, filed on Mar. 15, 2013, now Pat. No. 9,265,384.

(60) Provisional application No. 61/753,112, filed on Jan. 16, 2013.

(58) Field of Classification Search
USPC .................................. 222/38, 52, 36, 380
See application file for complete search history.

(56) References Cited

U.S. PATENT DOCUMENTS

| | | | | |
|---|---|---|---|---|
| 5,249,718 A | * | 10/1993 | Muderlak | B05B 11/3056 222/1 |
| 5,945,910 A | * | 8/1999 | Gorra | G08B 21/245 340/573.1 |
| 6,267,297 B1 | * | 7/2001 | Contadini | A61L 9/12 222/646 |
| 6,542,568 B1 | | 4/2003 | Howes, Jr. et al. | |
| 8,342,369 B2 | * | 1/2013 | Hsu | A47K 5/1202 222/309 |
| 8,573,443 B2 | * | 11/2013 | Natterer | B05B 9/043 222/173 |
| 9,265,384 B2 | * | 2/2016 | Wegelin | A47K 5/1205 |
| 2006/0144851 A1 | * | 7/2006 | Gonzalez De Echavarri | A61L 9/122 222/52 |
| 2009/0266842 A1 | | 10/2009 | Snodgrass | |
| 2010/0038452 A1 | * | 2/2010 | Lin | A61L 9/14 239/304 |
| 2014/0158714 A1 | * | 6/2014 | Snodgrass | A47K 5/1217 222/180 |
| 2014/0253336 A1 | * | 9/2014 | Ophardt | A47K 5/1202 340/573.1 |
| 2016/0128520 A1 | * | 5/2016 | Wegelin | A47K 5/1205 222/38 |

FOREIGN PATENT DOCUMENTS

| | | | | |
|---|---|---|---|---|
| GB | 2442471 A | * | 4/2008 | ........... E05B 1/0069 |
| JP | 2007061157 A | | 3/2015 | |
| WO | 2013/043461 A1 | | 3/2013 | |

* cited by examiner

POINT-OF-CARE HYGIENE COMPLIANCE MODULE

CROSS-REFERENCE TO RELATED APPLICATIONS

This application is a continuation of U.S. patent application Ser. No. 14/995,481 filed on Jan. 14, 2016, which is a divisional of U.S. patent application Ser. No. 13/833,525 filed on Mar. 15, 2013, which claims the benefit of U.S. Provisional Application No. 61/753,112 filed on Jan. 16, 2013, the contents of which are incorporated herein by reference.

TECHNICAL FIELD

The present invention generally relates to a hygiene compliance monitoring module for a dispensing container having an actuatable dispensing nozzle. Particularly, the present invention relates to a removable point-of-care hygiene compliance module that includes an actuator arm that is configured to be placed in operative contact with an actuatable dispensing nozzle of a dispensing container. More particularly, the present invention relates to a point-of-care hygiene compliance module that counts the number of dispensing nozzle actuations of a dispensing container as material is dispensed therefrom.

BACKGROUND OF THE INVENTION

Recently, the public has become increasingly concerned with disease and its transmission, and as such, there is an increased awareness of the importance of cleansing and hygiene in general. For example, with respect to the transmission of E. coli in the food services industry, the rhinovirus in elementary schools, and nosocomial diseases within healthcare facilities, numerous studies have cited hand hygiene as an effective measure to guard against disease transmission. In response, the healthcare industry, the food services industry, and the hotel and travel industries have been forced to examine their protocols and procedures to ensure that their personnel adopt hand-sanitizing habits that are efficacious in the prevention of disease transmission.

In response, as an effort to provide sufficient opportunities for individuals to have access to soap and sanitizers, many institutions and industries have provided numerous disposable or refillable (reusable) dispensing containers of sanitizer and/or soap to facilitate individuals in their efforts to sanitize and/or wash their hands. While the availability of such dispensing containers has increased the opportunities for individuals to wash and/or sanitize their hands, there is still a lack of compliance with predetermined hand-washing hygiene standards. However, to minimize the potential transmission of bacteria and/or viruses by hand washing and sanitization, full compliance with hygiene standards is required, as the failure of one individual to properly sanitize his or her hands can negate the efforts of others who come in contact with such individuals.

Unfortunately, to ensure compliance with predetermined hygiene standards, current hygiene compliance monitoring systems that are configured to track hygiene compliance of users require the use of one or more permanently-installed or mounted soap/sanitizer dispensers. Unfortunately, such permanently-installed dispensers are costly and typically require specialized training to administrate. Moreover, integrating hygiene compliance monitoring functionality provided by such permanently-installed dispensers into each disposable or refillable dispensing container would impart a substantial cost to the manufacture of otherwise inexpensive dispensing containers. Thus, the widespread use of such costly dispensing containers would limit their use, which is unwanted.

Therefore, there is a need for a point-of-care hygiene compliance module that is configured to be removably attached to a dispensing container, such as a refillable or disposable dispensing container or other portable dispensing container. In addition, there is a need for a self-powered point-of-care hygiene compliance module that is capable of being removably attached to the dispensing container. Furthermore, there is a need for a hygiene compliance module that is capable of being removably attached to a dispensing container and that is low-cost and user-friendly.

SUMMARY OF THE INVENTION

In light of the foregoing, it is one aspect of the present invention to provide a hygiene compliance module for a dispensing container.

It is another aspect of the present invention to provide a hygiene compliance module for a dispensing container that dispenses material through a dispensing nozzle when actuated, the hygiene compliance module comprising a housing that is adapted to be attached to the dispensing container; an actuation arm pivotably carried by said housing, said actuation arm adapted to operatively contact the dispensing nozzle; a switch carried by said housing, said switch in operative contact with said actuation arm, such that said switch is actuated when said actuation arm is actuated; a controller coupled to said switch; a memory unit coupled to said controller, said memory unit configured to store a count value that is updated when said switch is actuated; and a display coupled to said controller to display said count value, wherein when said actuation arm is actuated, it actuates the dispensing nozzle of the dispensing container to dispense material therefrom and actuates said switch to update said count value.

A further aspect of the present invention is to provide a hygiene compliance module for a dispensing container that dispenses material through a dispensing nozzle when actuated, the hygiene compliance module comprising a support frame adapted to carry the dispensing container therein; a housing attached to said support frame; an actuation arm pivotably carried by said housing, said actuation arm adapted to operatively contact the dispensing nozzle; a switch carried by said housing, said switch in operative contact with said actuation arm, such that said switch is actuated when said actuation arm is actuated; a controller coupled to said switch; a memory unit coupled to said controller, said memory unit configured to store a count value that is updated when said switch is actuated; and a display coupled to said controller to display said count value, wherein when said actuation arm is actuated, it actuates the dispensing nozzle of the dispensing container to dispense material therefrom and actuates said switch to update said count value.

Yet another aspect of the present invention is to provide a hygiene compliance module for a dispensing container that dispenses material through a dispensing nozzle when actuated, the hygiene compliance module comprising a housing that is adapted to be attached to the dispensing container; an actuation arm pivotably carried by said housing, said actuation arm adapted to operatively contact the dispensing nozzle; a switch carried by said housing, said switch in operative contact with said actuation arm, such that said switch is actuated when said actuation arm is actuated; a controller coupled to said switch; a memory unit coupled to said controller, said memory unit configured to store a count value that is updated when said switch is actuated; and a data port coupled to said controller, said data port adapted to communicate with a remote computing device to transfer said count value, wherein when said actuation arm is actuated, it actuates the dispensing nozzle of the dispensing container to dispense material therefrom and actuates said switch to update said count value.

BRIEF DESCRIPTION OF THE DRAWINGS

These and other features and advantages of the present invention will become better understood with regard to the following description and accompanying drawings where.

DETAILED DESCRIPTION OF THE INVENTION

Figure 1A:
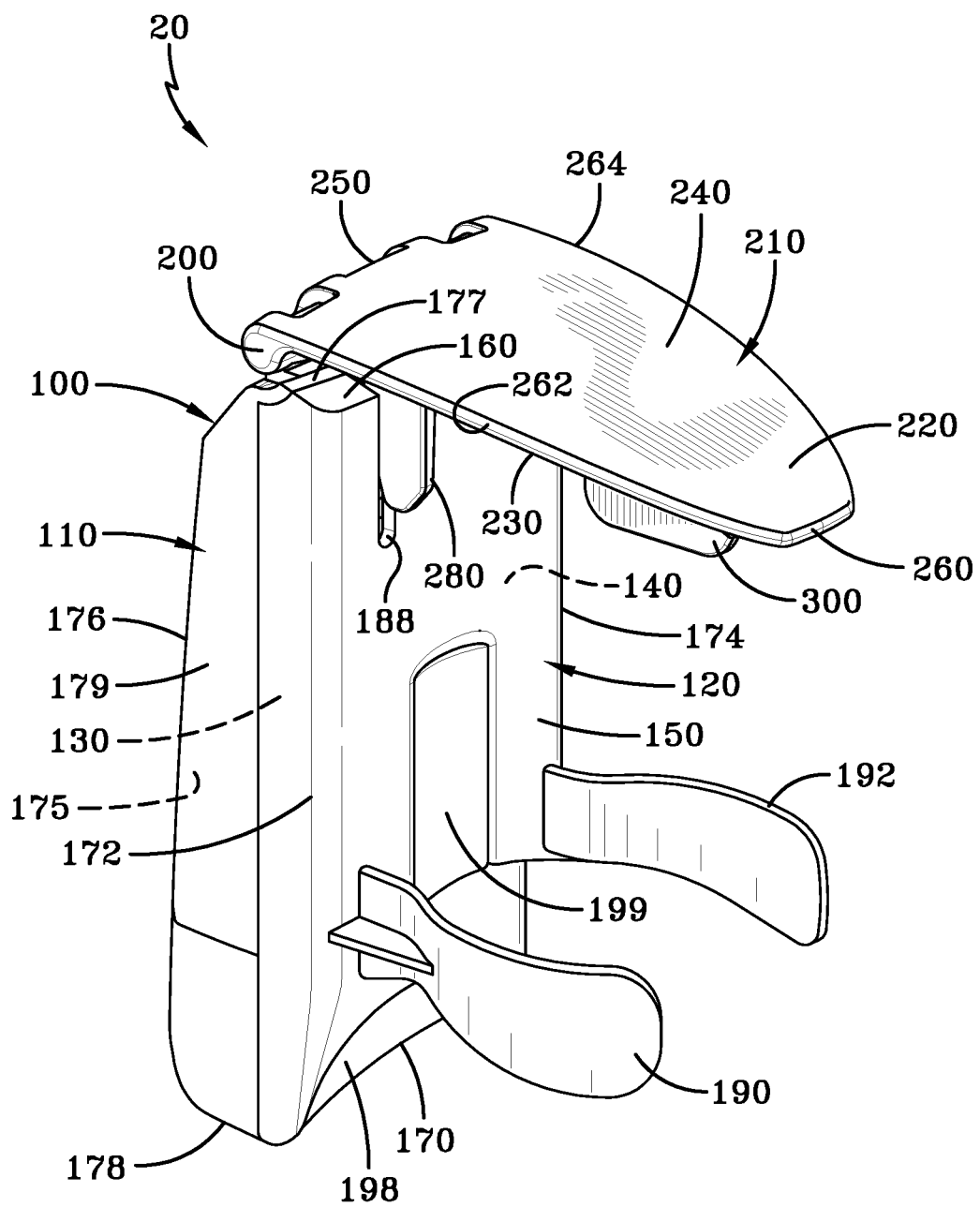
FIG. 1A is a perspective view of a point-of-care compliance module for use with a replaceable dispensing container in accordance with the concepts of the present invention.
Figure 1B:
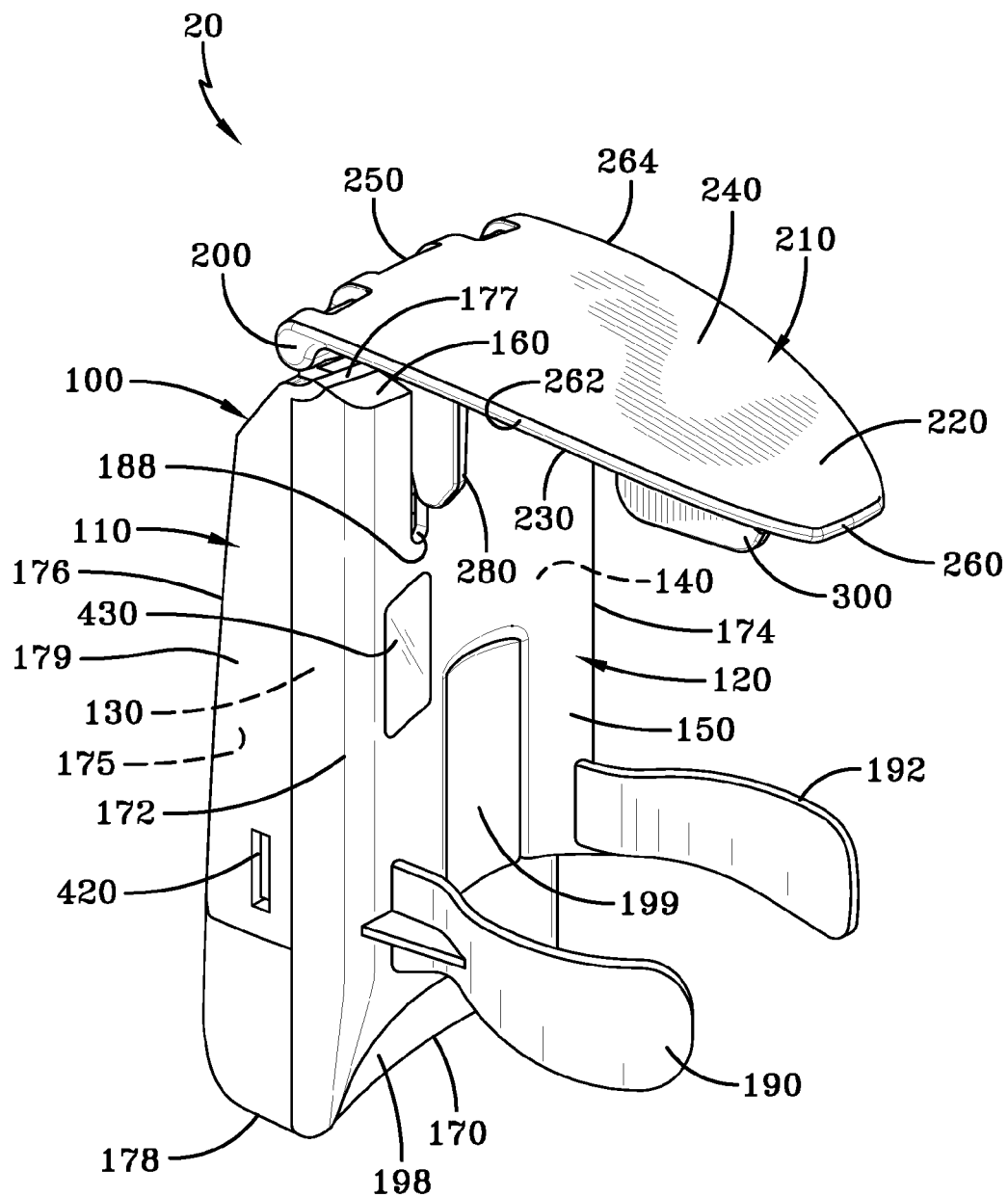
FIG. 1B is a perspective view of the point-of-care compliance module for use with a replaceable dispensing container showing a display and data port in accordance with the concepts of the present invention.
Figure 2:
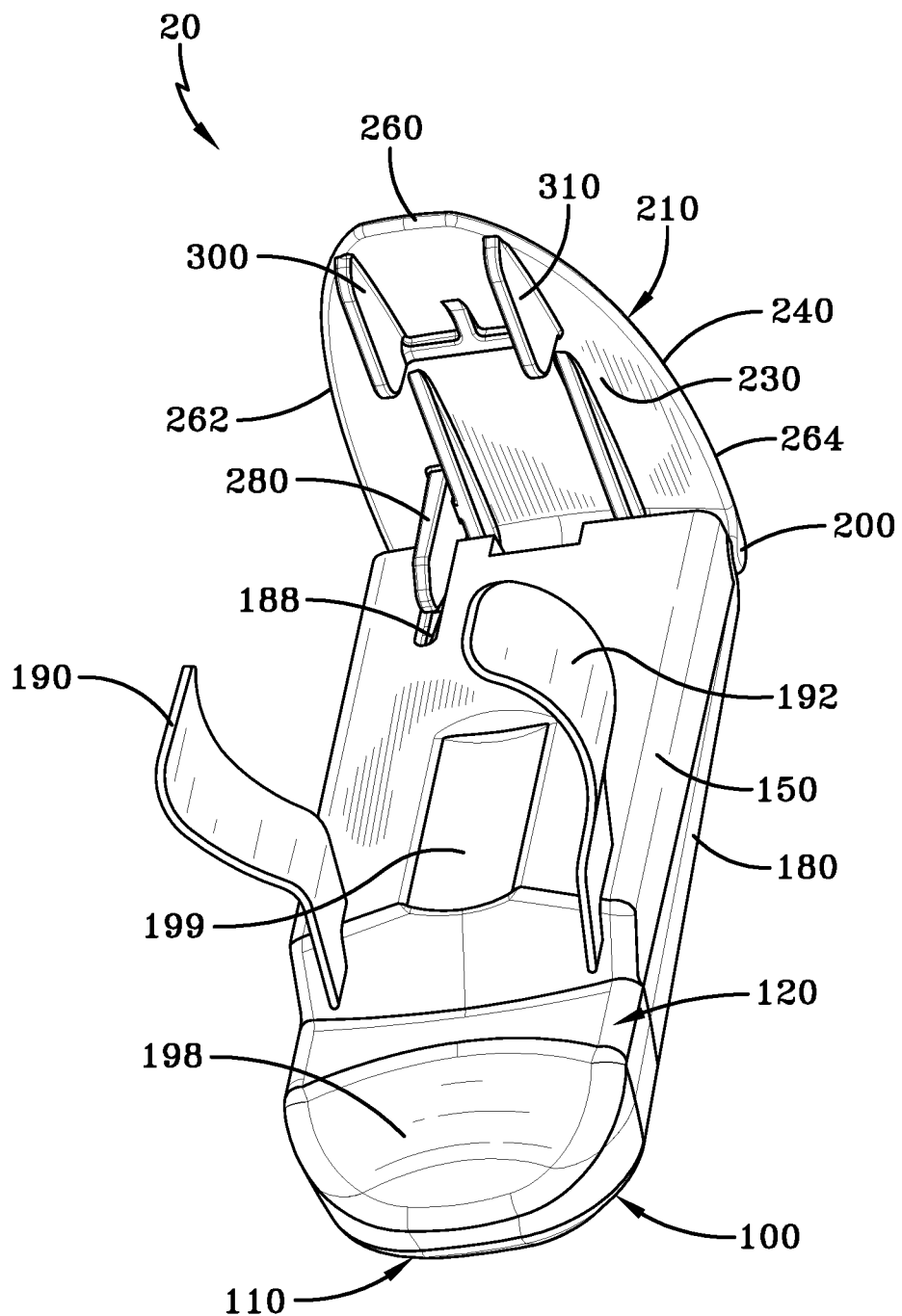
FIG. 2 is another perspective view of the point-of-care compliance module in accordance with the concepts of the present invention.
Figure 3:
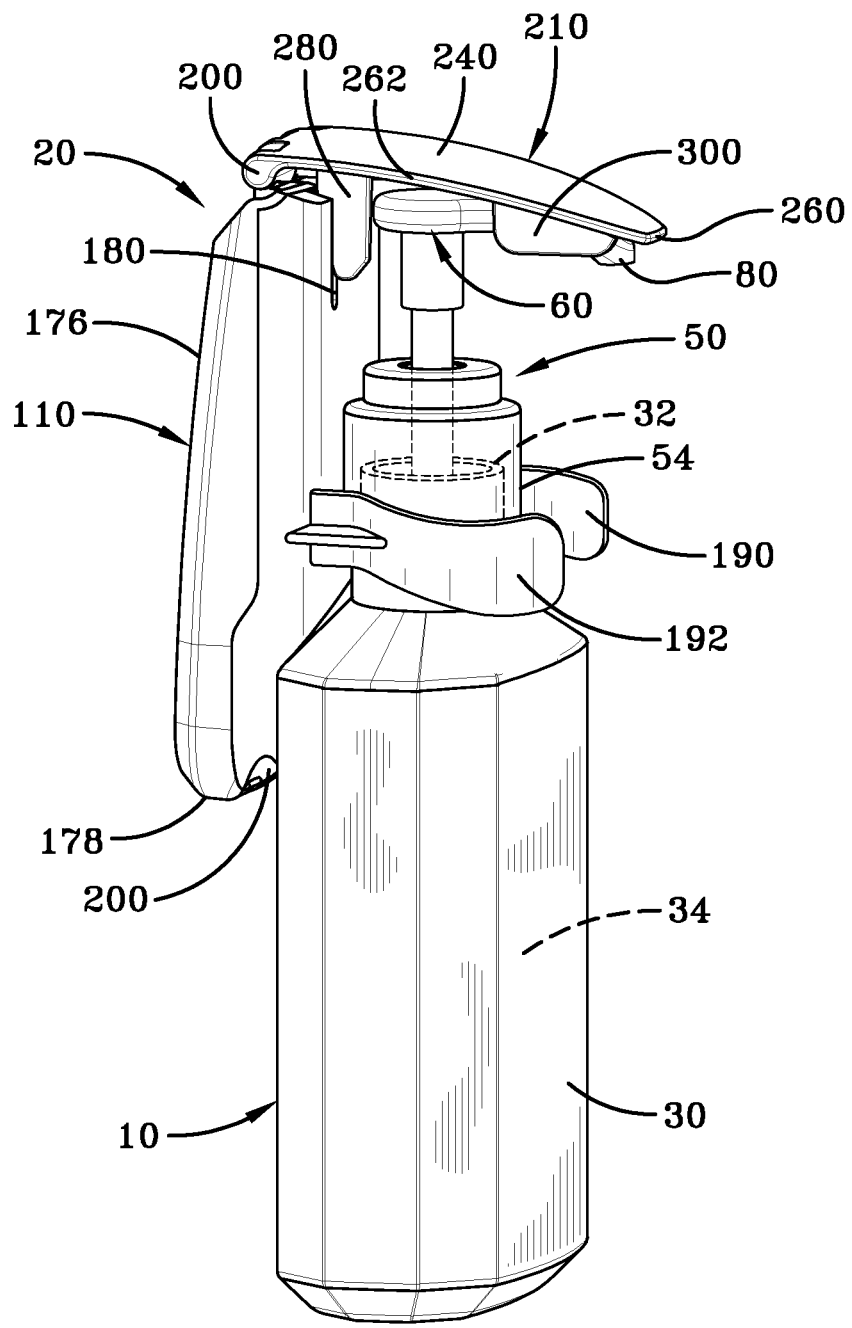
FIG. 3 is an elevational view of the point-of-care compliance module attached to the replaceable dispensing container in accordance with the concepts of the present invention.
Figure 4:
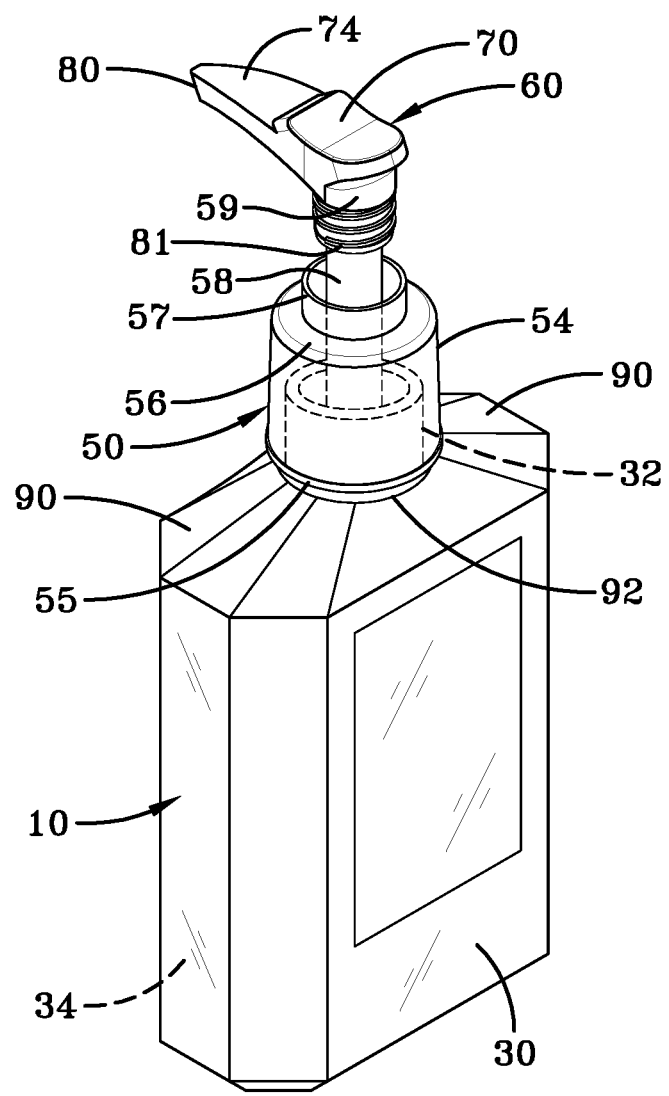
FIG. 4 is a perspective view of the replaceable dispensing container in accordance with the concepts of the present invention.

A point-of-care hygiene compliance module for a dispensing container 10 is generally referred to by the numeral 20, as shown in FIGS. 1-3 of the drawings. The dispensing container 10, shown clearly in FIG. 4, includes a hollow body 30 that holds any desired liquid material, such as soap, sanitizer, or moisturizer for example. In one aspect, it should be appreciated that the dispensing container 10 may comprise any suitable container, such as a portable dispensing container that is disposable or refillable for example. Extending from one end of the body 30 is a neck 32 that opens into a void 34 created by the hollow body 30. A pump assembly 50 is threadably attached to the neck 32 by a collar 54, so as to enable users to pump material out of the body 30 and into their hands when actuated. The collar 54 includes a base end 55 and an opposed top end 56, whereby an annular collar neck 57 extends from the top end 56 of the collar 54. Extending through the collar neck 57 is a tube 58 that is attached at one end to a nozzle neck 59 provided by a pump or dispensing nozzle 60 at one end, while the other end of the tube 58 is configured to be in fluid communication with the liquid material carried in the void 34 of the body 30 of the dispensing container 10.

Specifically, the pump nozzle or dispensing nozzle 60 includes a substantially planar actuation base 70 from which extends a nozzle end 74 that tapers as it extends downward and away from the actuation base 70 to a dispensing port 80. As such, the tapered and curved shape of the nozzle end 74 of the dispensing nozzle 60 allows the dispensed material to be directed downward toward the hands of a user when material is dispensed through the dispensing port 80. Also extending from the actuation base 70 at a substantially right angle is the nozzle neck 59 that includes a threaded section 81 that is configured to be threadably received by the collar neck 57 of the collar 54, so as to threadably lock the pump nozzle 60 thereto. To dispense material from the dispensing container 10, the pump nozzle 60 is depressed, forced downward, or otherwise actuated by pressing the engagement base 70 downward, whereupon liquid material is drawn from the tube 58 out of the dispensing container 10 by the pump assembly 50, and is dispensed from the dispensing port 80. That is, when the dispensing nozzle 60 is actuated, it moves relative to the collar 54 that is attached to the body 30.

It should also be appreciated that the body 30 of the dispensing container 10 may be configured to include a shoulder section 90 that extends radially away from an annular base edge 92 of the neck 32 in a substantially vertical or at least partially vertical direction.

Referring now to FIGS. 1-3, the hygiene compliance module 20 comprises a housing 100 having an outer section 110 and an inner section 120 that when joined together forms a cavity 130 therebetween. The inner section 120 includes an inner surface 140 and a substantially opposed outer surface 150 that are bounded by substantially opposed top and bottom edges 160 and 170 and by lateral edges 172 and 174. The outer section 110 includes an inner surface 175 and an outer surface 176 that are bounded by top and bottom edges 177 and 178 and by lateral edges 179 and 180. Disposed through the inner section 120 of the housing 100 proximate to the top edge 160 is a switch aperture 188. In addition, extending from a point proximate to each lateral edge 172 and 174 of the outer surface 150 of the inner section 120 of the housing 100 are respective retention arms 190 and 192. The retention arms 190,192 are dimensioned, shaped, and spaced apart so as to retain the collar 54 of the dispensing container 10 therebetween. That is, the retention arms 190, 192 secure the housing 100 of the hygiene compliance module 20 to the dispensing container 10 to enable operation of the hygiene compliance module 20. Alternatively, the retention arms 190,192 may be dimensioned to retain the body 30 or any other portion of the dispensing container 10 therebetween. Furthermore, it should also be appreciated that a portion of the outer surface 150 of the inner section 120 of the housing 100 that is proximate to the bottom edge 170 may include a concave or other contoured section or portion 198. In addition, the contoured section or portion 198 may also include not only the outer surface 150 of the inner section 120, but may include a portion of the of the outer section 110 of the housing 100. The contoured section 198 is dimensioned to accommodate a portion of the shoulder section 90 of the dispensing container 10, allowing the housing 100 of the hygiene compliance module 20 to be at least partially supported upon the dispensing container 10, while the retention arms 190,192 serve to hold the hygiene compliance module 20 to the dispensing container 10. It is also contemplated that a concave section 199 may be disposed in the outer surface 150 of the inner section 120 of the housing 100 of the hygiene compliance module 20 to accommodate the arcuate profile of the collar 54 of the dispensing container 10.

Attached to the top edge 177 of the outer section 110 of the housing 100 is a hinge 200 to which an actuator arm 210 is pivotably carried. The actuator arm 210 includes an elongated body 220 having an opposed inner and outer surface 230, 240 that is bounded by a bottom edge 250 that is attached to the hinge 200 and a top edge 260 and by contoured lateral edges 262 and 264. In one aspect, the actuator arm 210 is curved to have the same curvature as the nozzle end 74 of the dispensing container 10. Extending from the inner surface 230 of the actuator arm 210 at a point that is proximate the bottom edge 250 is a contact arm 280. The contact arm 280 is configured to be received through the switch aperture 188 that is disposed in the inner section 120 of the housing 100 and is configured to selectively contact a switch 284 that is carried within the mounting cavity 130 of the hygiene compliance module 20. Also extending from the inner surface 230 of the actuator arm 210 at a point proximate to the bottom edge 250 is a pair of spaced guides 300 and 310 that are separated at a distance, so as to allow the dispensing nozzle 60 of the dispensing container 10 to be received therebetween. In one aspect, the guides 300,310 may be spaced such that the dispensing nozzle 60 is retained therebetween by friction-fit or snap-fit for example. Alternatively, the guides 300,310 may be spaced sufficiently so that the dispensing nozzle 60 of the dispensing container is simply guided therebetween without being retained thereto when the actuator arm 210 is in operative contact with the dispensing nozzle 60.

Figure 5:
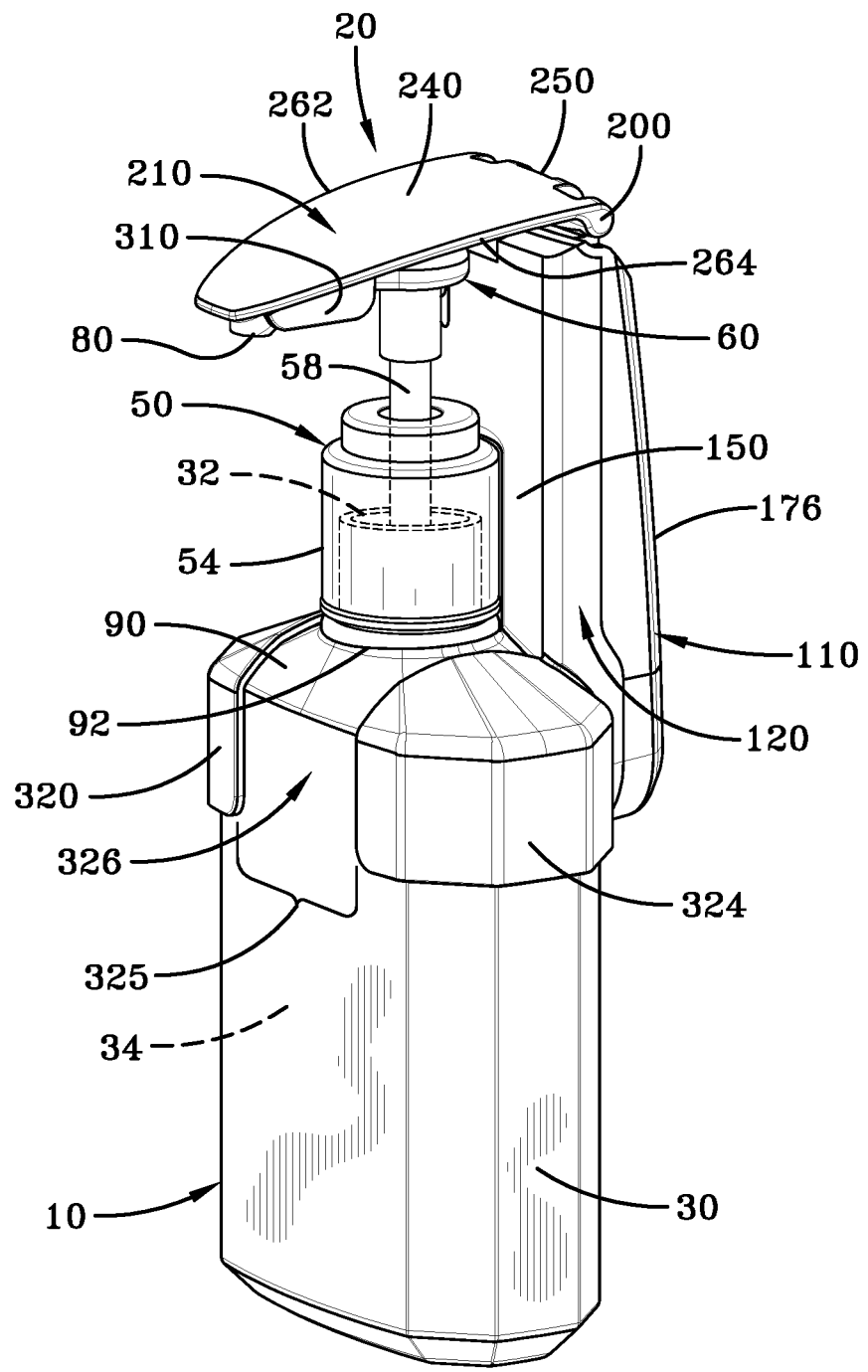
FIG. 5 is a perspective view of an alternative point-of-care compliance module attached to the replaceable dispensing container in accordance with the concepts of the present invention.

In another embodiment of the present invention, as shown in FIG. 5, the hygiene compliance module 20 may be configured so as to replace the retention arms 190,192 with shoulder receivers 320 and 324 respectively. Specifically, the shoulder receivers 320,324 extend from the outer surface 150 of the inner section 120 of the housing 100 of the hygiene compliance module 20 and are spaced apart by a gap 325 that allows the collar 54 of the dispensing container 10 to pass therethrough. In addition, the shoulder receivers 320,324 provide a receiving cavity 326 that is dimensioned to receive the shoulder section 90 of the dispensing container 10 therein, thus allowing the housing 100 to be supported upon the shoulder section 90 and retained to the dispensing container 10. Furthermore, the receiving cavity 326 of the shoulder receivers 320,324 may be configured so as to frictionally receive the shoulder section 90 of the dispensing container 10, allowing the hygiene compliance module 20 to be securely attached to the dispensing container 10, without falling off during operation of the hygiene compliance module 20.

Figure 6:
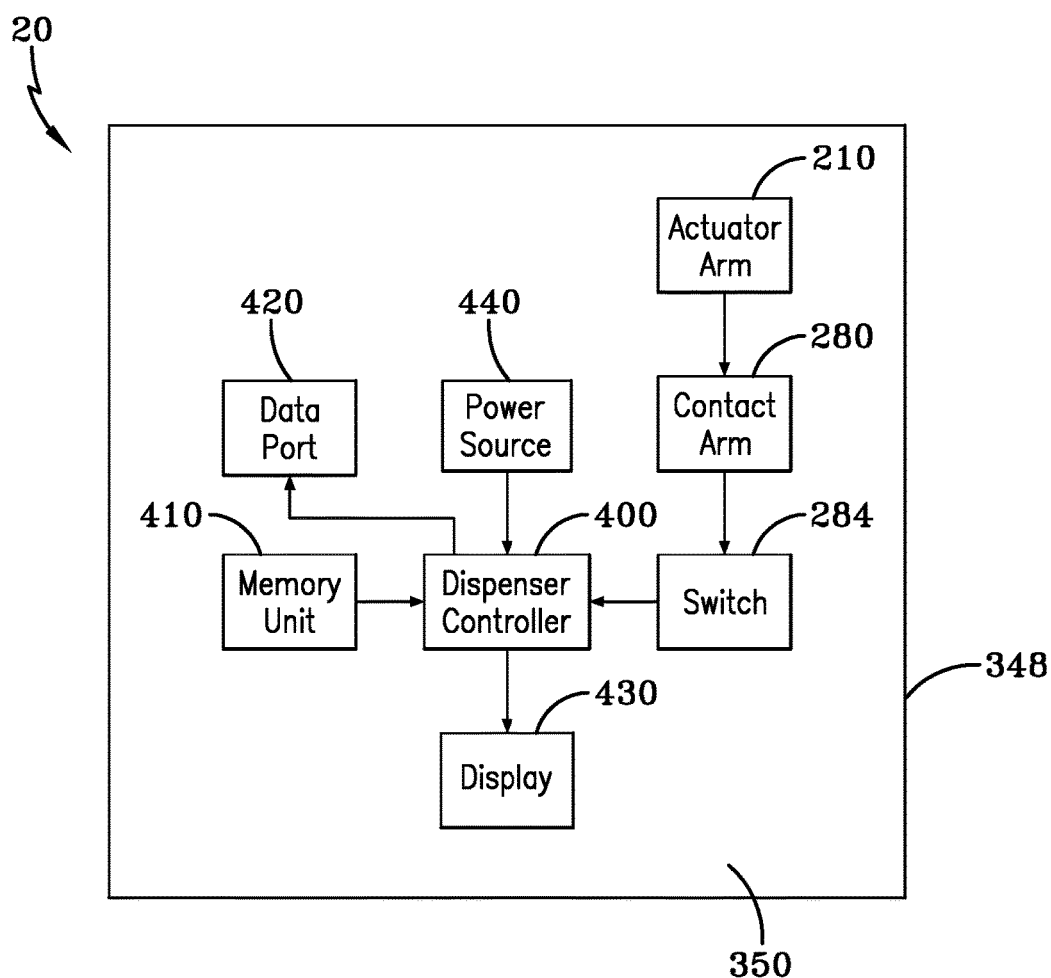
FIG. 6 is a block diagram of the electrical components carried by the point-of-care compliance module in accordance with the concepts of the present invention.

Continuing to FIG. 6, the hygiene compliance module 20 includes a monitoring device 348 that comprises a circuit board 350 carried within the cavity 130 of the housing 100. Carried upon the circuit board 350 of the monitoring device 348 is a dispenser controller 400 that includes the necessary hardware and software to carry out the functions of the hygiene compliance module 20 to be discussed. Coupled to the controller 400 is the switch 284 that is selectively actuated or triggered by the contact arm 280 when the actuator arm 210 is actuated in a manner to be discussed. That is, the switch 284 is carried upon the circuit board 350 so that it is in operative communication with the contact arm 280 when the actuator arm 210 is actuated. In one aspect, the switch 284 may comprise any suitable switching device, such as a microswitch for example.

Coupled to the controller 400 is a memory unit 410 that may comprise any suitable volatile or non-volatile memory and is configured to store a count value that is updated by the controller 400 each time the switch 284 is actuated by the actuator arm 210. It should be appreciated that the count value may be used to compute other usage data associated with the consumption of the material in the dispensing container 10. Also coupled to the controller 400 is a data port 420, which may comprise any suitable wired or wireless communication interface, such as an Ethernet-, WIFI-, or BLUETOOTH-based communication interface for example. Alternatively, the data port 420 may comprise data tag-based communication technology, including NFC or RFID, for example.

As such, any suitable computing system may be interfaced with the controller 400 via the data port 420 to perform various functions at the hygiene compliance module 20, including the communication and transfer (i.e. acquiring) of the count value data stored at the memory unit 410.

The hygiene compliance module 20 may also include a display 430, such as an LCD (liquid crystal display) display that is coupled to the controller 400. The display 430 is configured to display the count value that is stored at the memory unit 410, as well as various other status information associated with the operation of the hygiene compliance module 20. It should also be appreciated that the data port 420 and the display 430 may be carried by the housing 100, as shown in FIG. 1B, for the convenience of the user. Finally, the hygiene compliance module 20 is powered by a power source 440, such as an A.C. (alternating current) or D.C. (direct current) power source, provided by a standard electrical outlet, battery, or photovoltaic cell for example. In one aspect, the power source may comprise a photovoltaic cell. In another aspect, it is contemplated that the count value stored at the memory unit 410 may be reset by actuating the actuator arm 210 in a predetermined sequence.

Figure 7:
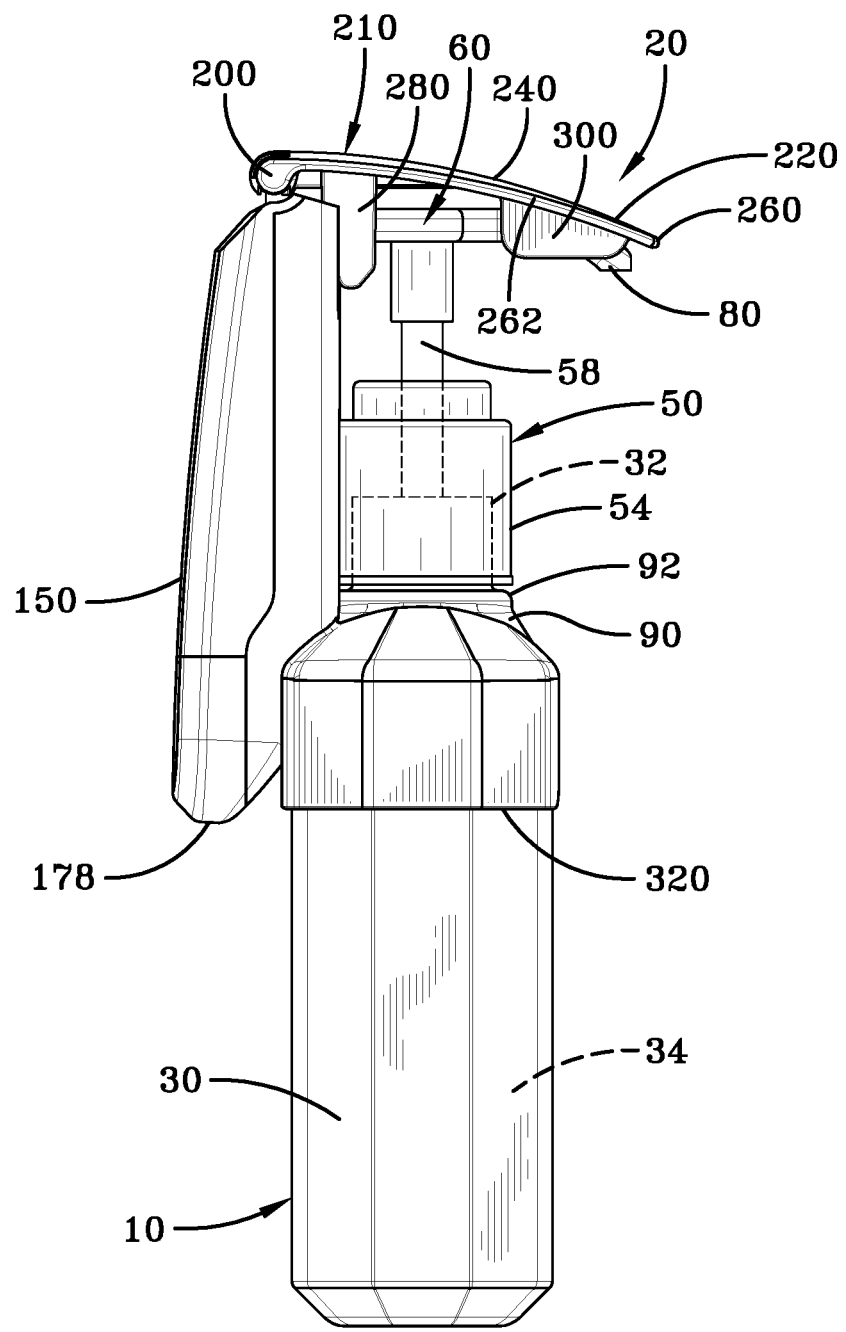
FIG. 7 is an elevational view of the alternative point-of-care compliance module showing the actuator arm in its normal resting position in accordance with the concepts of the present invention.
Figure 8:
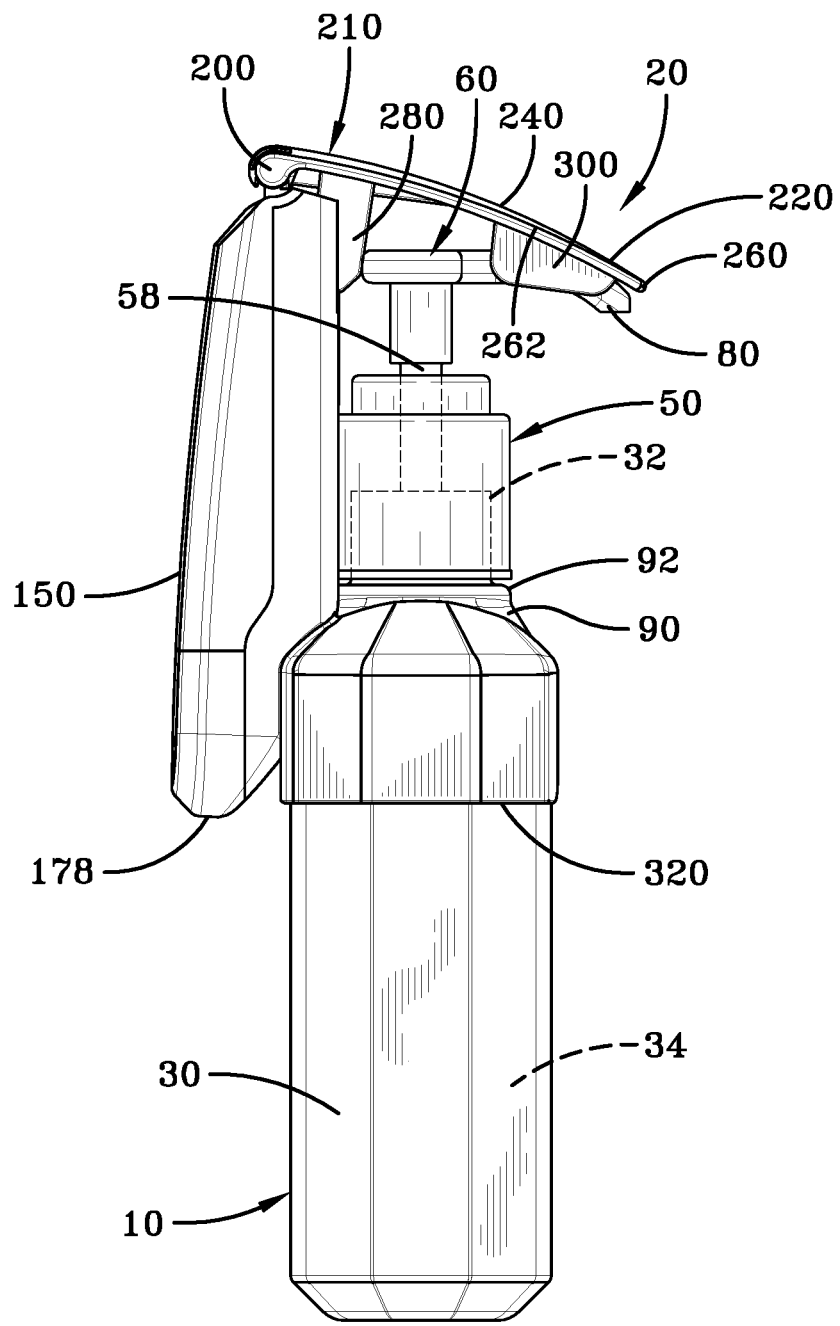
FIG. 8 is an elevational view of the alternative point-of-care compliance module showing the actuator arm in a depressed or actuated position, so as to dispense material from the dispensing container in accordance with the concepts of the present invention.

Thus, with the structural components of the hygiene compliance module 20 set forth, the following discussion presents the steps for placing the hygiene compliance module 20 into operation. Initially, the housing 100 is removably attached to the dispensing container 10 by placing the collar 54 of the dispensing container 10 between the retention arms 190 and 192. In addition, in the case where the housing 100 includes a contoured section 198, the shoulder section 90 of the dispensing container 10 may be at least partially received by the contoured section 198. In addition, in the alternative embodiment of the hygiene compliance module 20, where the shoulder retainers 320,324 are used in lieu of the retention arms 190,192, the shoulder section 90 of the dispensing container 10 is received within the cavity 326, as shown in FIG. 7. Once the hygiene compliance module 20 is attached to the dispensing container 10, the actuator arm 210 is rotated such that the dispensing nozzle 60 of the dispensing container 10 is disposed between the guides 300,310. It should be appreciated that the dispensing nozzle 60 may be retained between the guides 300,310, as previously discussed. After the actuator arm 210 is disposed against or otherwise in operative contact with the dispensing nozzle 60 of the dispensing container 10, the user depresses or otherwise forces actuator arm 210 downward, as shown in FIG. 8. This causes the actuator arm 210 to rotate or pivot downward, causing the contact arm 280 to operatively contact and actuate the switch 284 as the dispensing nozzle 60 simultaneously or nearly simultaneously actuates the pump assembly 50 of the dispensing container 10 to dispense material from the nozzle port 80. The actuation of the switch 284 causes the controller 400 to update the count value stored at the memory unit 410, that represents the total number of actuations of dispensing nozzle 60 that have occurred since the count value was last reset. As previously discussed, it is also contemplated that the count value stored at the memory unit 410 may be reset by actuating the actuator arm 210 in a predetermined sequence or by actuating a reset switch coupled to the controller 400.

Figure 9:
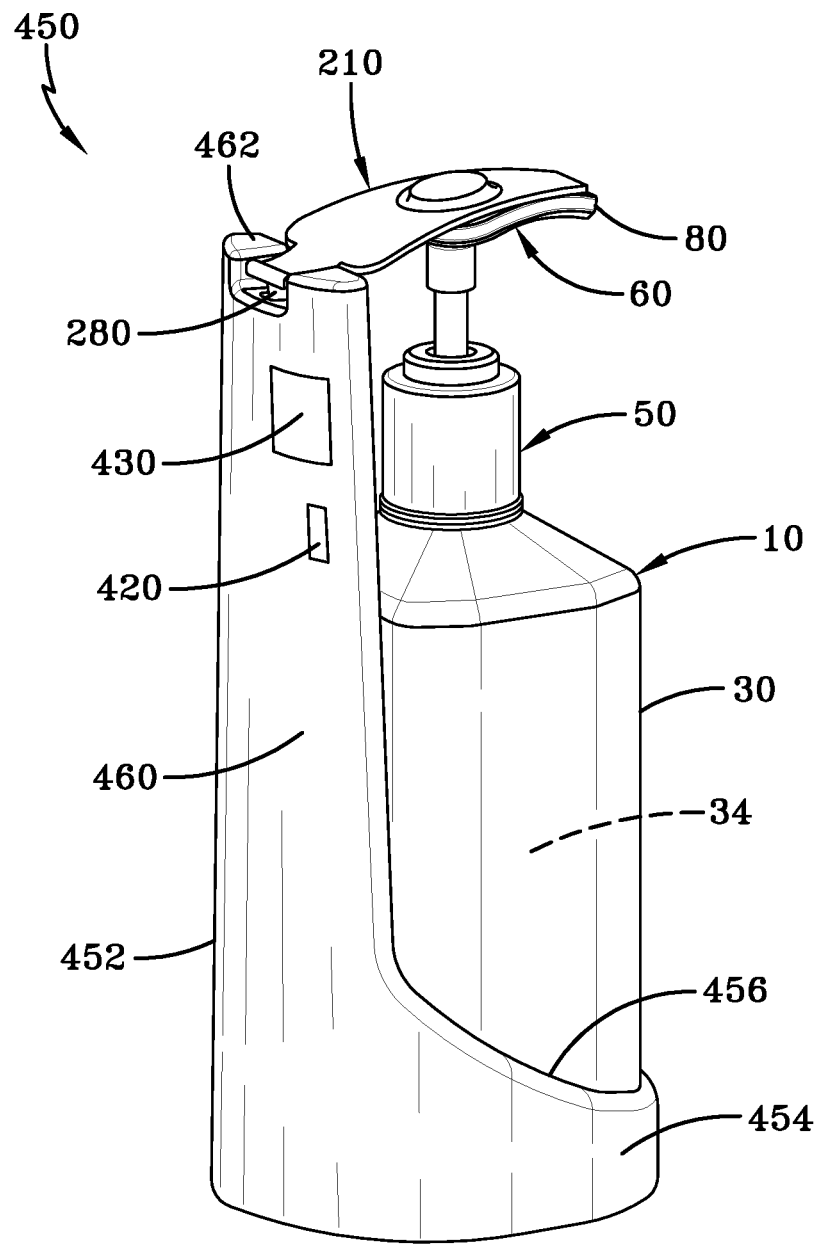
FIG. 9 is a perspective view of another alternative point-of-care compliance module attached to the replaceable dispensing container in accordance with the concepts of the present invention.

In another embodiment of the present invention a point of care (POC) hygiene compliance module is generally referred to by the numeral 450, as shown in FIG. 9 of the drawings. Specifically, the compliance module 450 includes a base housing 452 that is configured to rest on any suitable flat surface, such as a table for example. The base housing 452 includes a retainer section 454 that includes a receiving cavity 456 that is dimensioned to receive a portion of the body 30 of the dispensing container 10 therein, so as to retain the dispensing container 10 to the base housing 452. Extending from the retainer section 454 is a neck 460 that is terminated at an end 462, which pivotably carries the actuator arm 210, as previously discussed. Carried within the base housing 452 is the monitoring device 348 as previously discussed, such that the switch 284 is operatively coupled to the actuator arm 210 via contact arm 280. Thus, when the actuator arm 210 is placed adjacent to the dispensing nozzle 60 and pressed downward, the contact arm 280 is moved to actuate the switch 284 of the monitoring device 348 as the dispensing nozzle 60 is compressed so that material from the dispensing port 80 is dispensed therefrom. Accordingly, the actuation of the switch 284 increments or updates a count value stored at the controller 400, as previously discussed. Furthermore, the count value may be presented for viewing on the display 430 or may be acquired remotely via the data port 420 that is provided by the base housing 452 via a wired or wireless connection, as previously discussed.

Figure 10:
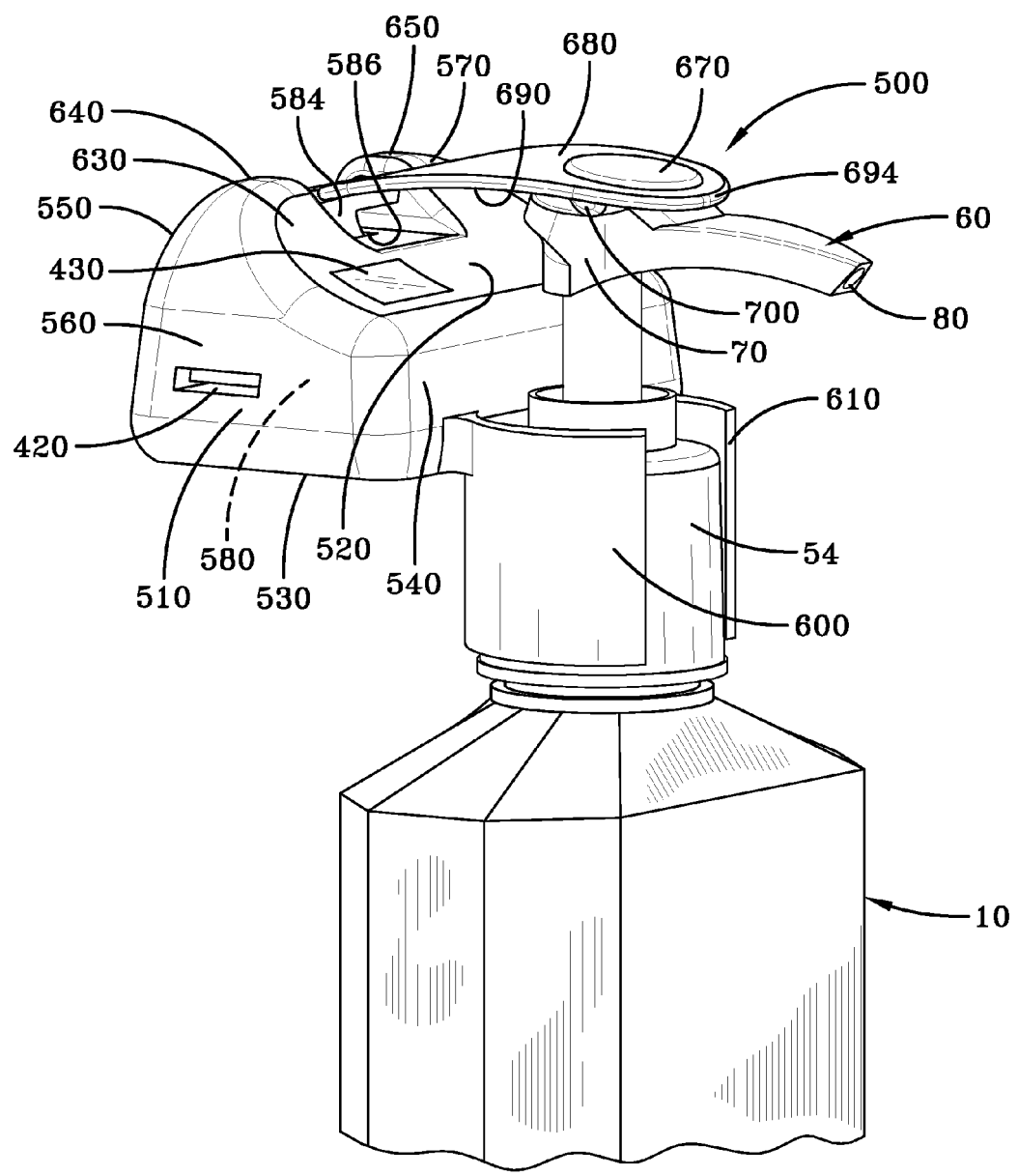
FIG. 10 is a perspective view of still another alternative point-of-care compliance module attached to a replaceable dispensing container in accordance with the concepts of the present invention.

In yet another embodiment of the present invention a point of care hygiene compliance module is generally referred to by the numeral 500, as shown in FIG. 10 of the drawings. The compliance module 500 includes a housing 510 having a top section 520 that is opposite to a bottom section 530 and substantially opposed front and rear sections 540,550 and substantially opposed lateral sections 560,570 that together define a cavity 580 therein. The hygiene compliance module 500 also includes a pair of spaced retention arms 600 and 610 that are dimensioned to receive and retain therebetween the collar 54 of the dispensing container 10 previously discussed. Specifically, the retention arms 600,610 may be curved or otherwise contoured to facilitate their ability to retain the collar 54. As such, when the collar 54 of the dispensing container 10 is retained between the retention arms 600,610 the compliance module 500 is fully supported by and retained to the dispensing container 10.

Continuing, the top section 520 includes an outer surface 630 from which extends a pair of spaced support sections 640,650. Pivotably attached between the support sections 640,650 is an elongated actuator arm 670 that includes a top surface 680 that is opposite to a bottom surface 690 and that is bounded by a base edge 692 and an outer edge 694. Extending from the bottom surface 90 of the actuator arm 670 is a protrusion 700 that is dimensioned to contact the actuation base 70 of the dispensing nozzle 60 of the dispensing container 10.

Carried within the cavity 580 of the housing 510 is the circuit board 350 previously discussed with regard to the hygiene compliance module 20. As such, the actuator arm 670 includes an actuation tab 584 that moves through a tab aperture 586 that is disposed through the housing 510. Specifically, the actuation tab 584 is configured to actuate the switch 284 when the actuator arm 670 pivots or rotates when it is depressed when it is desired that material be dispensed.

During the operation of the compliance module 500, it is attached to the dispensing container 10, such that the retention arms 600,610 retain the collar 54 of the dispensing container 10 therebetween. That is, the retention arms 600,610 are configured to frictionally or compressively retain the collar 54 of the dispensing container 10 therebetween so as to support and carry the compliance module 500. Next, the actuator arm 670 is positioned so that the protrusion 700 is in contact upon the actuation base 70 of the dispensing nozzle 60. Thus, compressing or otherwise forcing the actuator arm 670 downward causes the actuator arm 670 to rotate downward as the dispensing nozzle 60 is compressed, and as a result, the switch 284 is actuated to update the count value as material is dispensed from the dispensing port 80 of the dispensing container 10. It should also be appreciated that the housing 510 may also include the data port 420 and the display 430, as previously discussed. It should also be appreciated that the housing 510 may include a base in which the dispensing container 10 can sit upon or inside of.

Figures 11, 12:
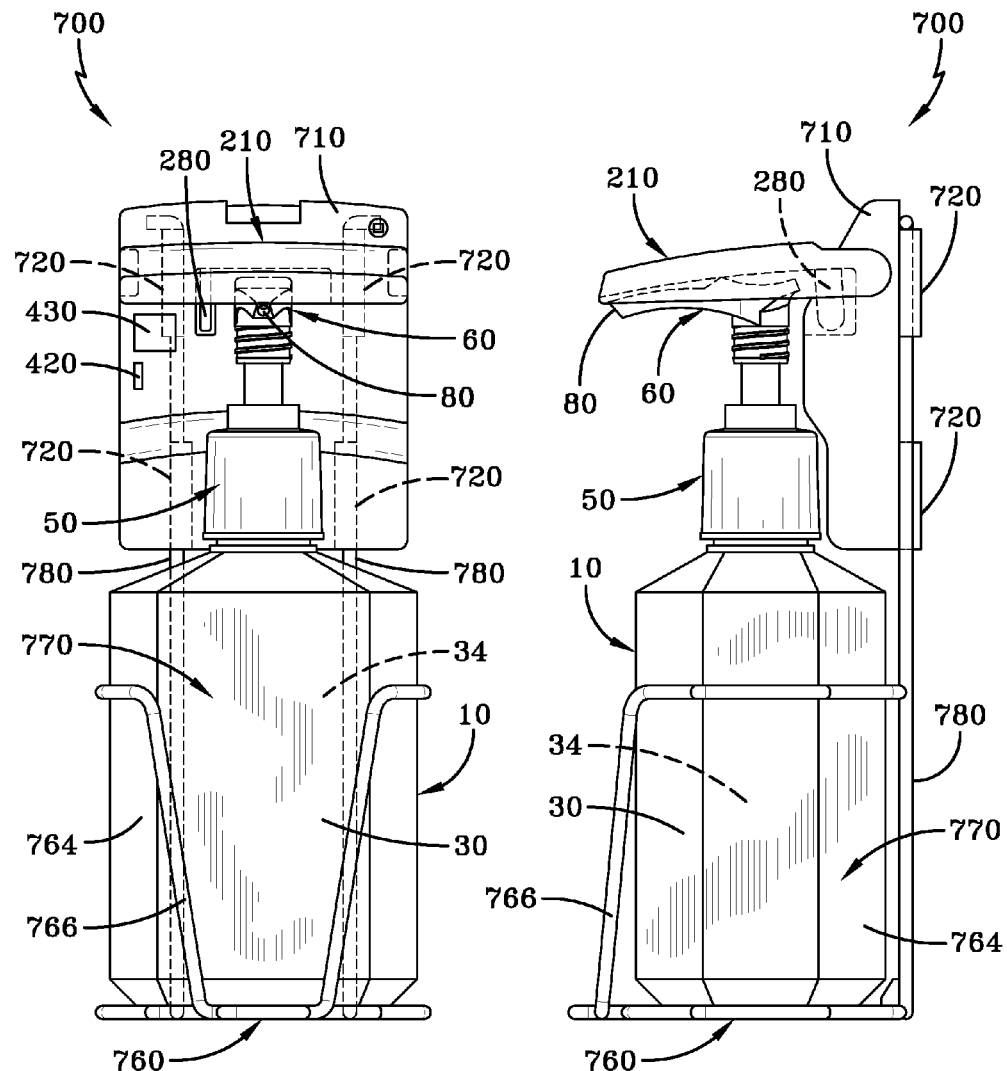
FIG. 11 is a front elevational view of yet another embodiment of a point-of-care compliance module that is attached to frame that is configured to selectively receive a replaceable dispensing container in accordance with the concepts of the present invention.
FIG. 12 is a side elevational view of the point-of-care compliance module shown in FIG. 11 in accordance with the concepts of the present invention.

In another embodiment of the present invention a point of care hygiene compliance module is generally referred to by the numeral 700, as shown in FIGS. 11-12 of the drawings. Specifically, the hygiene compliance module 700 includes a housing 710 that includes one or more attachment clips or tabs 720 and an actuator arm 210 that is pivotably attached thereto. The housing 710 carries the monitoring device 348 such that the actuator arm 210 is operatively coupled to the switch 284 via the contact arm 280 that is carried by the actuator arm 210. The housing 710 is configured to be selectively attached to a support frame 760, such as a wire frame, via the one or more attachment clips or tabs 720. Specifically, the frame 760 includes retaining arms 764 and 766 that serve to form a receiving aperture 770 therebetween that is configured to receive the body 30 of the dispensing container 10 therein. Extending substantially vertically from the retaining arms 764,766 are one or more support arms 780 that are provided to allow the housing 700 to be selectively attached thereto via the one or more attachment clips or tabs 720.

Thus, to place the compliance module 700 into operation, the housing 710 is attached to the one or more support arms 780 of the support frame 760 via the one or more attachment clips or tabs 720. Once the housing 710 of the compliance module 700 is attached to the support frame 760, the dispensing container 10 is placed within the receiving aperture 770 where it is held in place by the retaining arms 764,766. Next, the actuator arm 210 is moved so that it is in operative contact with the dispensing nozzle 60, such that when the actuator arm 210 is depressed, the dispensing nozzle 60 is compressed, and material is dispensed from the dispensing port 80. In addition, the movement of the actuator arm 210 also causes the switch 284 to be actuated or triggered via the contact arm 280, so as to increment or otherwise update a count value stored at the controller 400. In addition, the count value may be presented upon the display 430 and may be accessed by a remote computing device via the data port 420 through a wired or wireless connection.

It will, therefore, be appreciated that one advantage of one or more embodiments of the present invention is that a point-of-care compliance module can be removably attached to a disposable or refillable dispensing container that carries any desired liquid material, such as soap, sanitizer, or moisturizer, for example. Another advantage of the present invention is that a point-of-care compliance module is able to be quickly and readily attached to a dispensing container without the use of tools. Still another advantage of the present invention is that a point-of-care compliance module for a dispensing container can be manufactured with low cost. Yet another advantage of the present invention is that a point-of-care compliance module is configured so that it can be attached to dispensing containers of various shapes and sizes. An additional advantage of the present invention is that a point-of-care compliance module utilizes a pivoting actuator arm that is configured to operatively contact a pump nozzle of a dispensing container and to update a count value when the pump nozzle is actuated as material is dispensed therefrom.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A hygiene compliance module for a dispensing container that dispenses material through a dispensing nozzle when actuated, the hygiene compliance module comprising:
a housing having a receiving cavity for receiving a portion of the dispensing container therein;
an actuation arm pivotably carried by the housing, the actuation arm having a contact surface that is adapted to operatively contact the dispensing nozzle, the actuation arm comprising a first guide and a second guide attached to the contact surface, the first guide and the second guide spaced apart so as to receive the dispensing nozzle of the dispensing container, the dispensing nozzle disposed on a first side of the contact surface;
a switch carried by the housing and disposed on the first side of the contact surface, the switch in operative contact with the actuation arm, such that the switch is actuated when the actuation arm is actuated;
a controller coupled to the switch;
a memory unit coupled to the controller, the memory unit configured to store a count value that is updated when the switch is actuated; and
a communication interface coupled to the controller to communicate the count value to a remote computing device;
wherein when the actuation arm is actuated, the actuation arm actuates the dispensing nozzle of the dispensing container to dispense material therefrom, and actuates the switch to update the count value.

2. The hygiene compliance module of claim 1, wherein the communication interface comprises a wired connection.

3. The hygiene compliance module of claim 1, wherein the communication interface comprises a wireless connection.

4. The hygiene compliance module of claim 1, wherein the first guide extends parallel to the second guide.

5. The hygiene compliance module of claim 1, wherein the housing comprises a first retention arm and a second retention arm, the first retention arm and the second retention arm spaced apart to define the receiving cavity so as to receive the portion of the dispensing container therein.

6. A hygiene compliance module for a dispensing container that dispenses material through a dispensing nozzle when actuated, the hygiene compliance module comprising:
a housing having a receiving cavity for receiving a portion of the dispensing container therein, the housing defining a switch aperture;
an actuation arm attached to the housing, the actuation arm adapted to operatively contact the dispensing nozzle when the actuation arm is actuated;
a contact arm attached to the actuation arm, the contact arm received within the switch aperture when the actuation arm is actuated; and
a monitoring device comprising a switch disposed within the housing;
wherein when the actuation arm is actuated:
the actuation arm actuates the dispensing nozzle of the dispensing container to dispense material therefrom; and
the contact arm is received within the switch aperture and actuates the switch, the monitoring device configured to track a count value that is updated when the switch is actuated.

7. The hygiene compliance module of claim 6, wherein the actuation arm has a contact surface that is adapted to operatively contact the dispensing nozzle when the actuation arm is actuated.

8. The hygiene compliance module of claim 7, wherein the contact arm is attached to the contact surface.

9. The hygiene compliance module of claim 6, wherein the actuation arm is pivotably attached to the housing.

10. The hygiene compliance module of claim 6, wherein:
when the actuation arm is actuated and in a first position, the contact arm is in contact with the switch; and
when the actuation arm is not actuated and in a second position, the contact arm is not in contact with the switch.

11. The hygiene compliance module of claim 6, wherein the housing comprises a first retention arm and a second retention arm, the first retention arm and the second retention arm spaced apart to define the receiving cavity so as to receive the portion of the dispensing container therein.

12. The hygiene compliance module of claim 11, the first retention arm and the second retention arm spaced a distance apart from the actuation arm.

13. A hygiene compliance module for a dispensing container that dispenses material through a dispensing nozzle when actuated, the hygiene compliance module comprising:
- a housing having a receiving cavity for receiving a portion of the dispensing container therein;
- an actuation arm attached to the housing, the actuation arm adapted to operatively contact the dispensing nozzle; and
- a monitoring device comprising:
  - a switch disposed within the housing, the switch in operative contact with the actuation arm, such that the switch is actuated when the actuation arm is actuated;
  - a controller coupled to the switch; and
  - a memory unit coupled to the controller, the memory unit configured to store a count value that is updated when the switch is actuated;
- wherein when the actuation arm is actuated, the actuation arm actuates the dispensing nozzle of the dispensing container to dispense material therefrom and actuates the switch to update the count value.

14. The hygiene compliance module of claim 13, wherein the housing defines an interior within which the monitoring device is received.

15. The hygiene compliance module of claim 13, wherein:
- when the actuation arm is actuated and in a first position, the actuation arm is in contact with the switch; and
- when the actuation arm is not actuated and in a second position, the actuation arm is not in contact with the switch.

16. The hygiene compliance module of claim 13, wherein the actuation arm has a contact surface that is adapted to operatively contact the dispensing nozzle when the actuation arm is actuated.

17. The hygiene compliance module of claim 16, wherein the dispensing nozzle is disposed on a first side of the contact surface.

18. The hygiene compliance module of claim 17, wherein the switch is disposed on the first side of the contact surface.

19. The hygiene compliance module of claim 13, wherein the housing comprises a first retention arm and a second retention arm, the first retention arm and the second retention arm spaced apart to define the receiving cavity so as to receive the portion of the dispensing container therein.

20. The hygiene compliance module of claim 13, wherein the communication interface comprises at least one of a wired connection or a wireless connection.

* * * * *